US00PP30803P2

(12) United States Plant Patent
Sakazaki

(10) Patent No.: US PP30,803 P2
(45) Date of Patent: Aug. 13, 2019

(54) ***CALIBRACHOA* PLANT NAMED 'USCAL51505'**

(50) Latin Name: ***Calibrachoa* sp.**
Varietal Denomination: USCAL51505

(71) Applicant: Ushio Sakazaki, Shiga (JP)

(72) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 15/998,150

(22) Filed: Jul. 10, 2018

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
See application file for complete search history.

*Primary Examiner* — Annette H Para
(74) *Attorney, Agent, or Firm* — C. A. Whealy

(57) ABSTRACT

A new and distinct *Calibrachoa* plant named 'USCAL51505', characterized by its compact, upright to outwardly spreading and mounding to trailing plant habit; moderately vigorous growth habit; freely branching habit; dense and bushy appearance; early and freely flowering habit; double flowers with pale yellow-colored petals and petaloids; and good garden performance.

1 Drawing Sheet

Botanical designation: *Calibrachoa* sp.
Cultivar denomination: 'USCAL51505'.

BACKGROUND OF THE INVENTION

The present invention relates to a new and distinct cultivar of *Calibrachoa* plant, botanically known as *Calibrachoa* sp. and hereinafter referred to by the name 'USCAL51505'.

The new *Calibrachoa* plant is a product of a planned breeding program conducted by the Inventor in Higashiomi, Shiga, Japan and Bonsall, Calif. The objective of the breeding program is to create new uniform and freely-branching *Calibrachoa* plants with unique and attractive flower forms and colors and good garden performance.

The new *Calibrachoa* plant originated from a cross-pollination conducted by the Inventor in Higashiomi, Shiga, Japan on May 26, 2012 of a proprietary seedling selection of *Calibrachoa* sp. identified as code number CJ08-07, not patented, as the female, or seed, parent with a proprietary seedling selection of *Calibrachoa* sp. identified as code number CC016-01, not patented, as the male, or pollen, parent. The new *Calibrachoa* plant was discovered and first selected by the Inventor as a single flowering plant within the progeny of the stated cross-pollination in a controlled greenhouse environment in Bonsall, Calif. on Jun. 5, 2013.

Asexual reproduction of the new *Calibrachoa* plant by vegetative terminal cuttings in a controlled greenhouse environment in Bonsall, Calif. since Jun. 6, 2013 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'USCAL51505'. These characteristics in combination distinguish 'USCAL51505' as a new and distinct *Calibrachoa* plant:

1. Compact, upright to outwardly spreading and mounding to trailing plant habit.
2. Moderately vigorous growth habit.
3. Freely branching habit; dense and bushy appearance.
4. Early and freely flowering habit.
5. Double flowers with pale yellow-colored petals and petaloids.
6. Good garden performance.

Plants of the new *Calibrachoa* differ primarily from plants of the female parent selection in the following characteristics:

1. Plants of the new *Calibrachoa* are more mounding than and not as upright as plants of the female parent selection.
2. Plants of the new *Calibrachoa* and the female parent selection differ in flower color as flowers of plants of the female parent selection are lighter yellow in color.

Plants of the new *Calibrachoa* differ primarily from plants of the male parent selection in the following characteristics:

1. Plants of the new *Calibrachoa* are more mounding than and not as creeping as plants of the male parent selection.
2. Plants of the new *Calibrachoa* have double-type flowers whereas plants of the male parent selection have single-type flowers.
3. Plants of the new *Calibrachoa* and the male parent selection differ in flower color as flowers of plants of the male parent selection are darker yellow in color.

Plants of the new *Calibrachoa* can be compared to plants of the *Calibrachoa* sp. 'KLECA15290', not patented. In side-by-side comparisons, plants of the new *Calibrachoa* differ primarily from plants of 'KLECA15290' in the following characteristics:

1. Plants of the new *Calibrachoa* are more vigorous than plants of 'KLECA15290'.
2. Plants of the new *Calibrachoa* have fully double flowers whereas plants of 'KLECA15290' have semi-double flowers.

Plants of the new *Calibrachoa* can also be compared to plants of the *Calibrachoa* sp. 'KLECA11226', not patented. In side-by-side comparisons, plants of the new *Calibrachoa* differ primarily from plants of 'KLECA11226' in the following characteristics:

1. Plants of the new *Calibrachoa* have fully double flowers whereas plants of 'KLECA11226' have semi-double flowers.
2. Plants of the new *Calibrachoa* and 'KLECA11226' differ in flower color as flowers of plants of 'KLECA11226' are yellow and rose pink in color.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet is a side perspective view of a typical flowering plant of 'USCAL51505' grown in a container.

The photograph at the top of the sheet is a close- up view of a typical flowering plant of 'USCAL51505'.

DETAILED BOTANICAL DESCRIPTION

The aforementioned photographs and following observations and measurements describe plants grown during the late winter and early spring in 11.5-cm containers in an acrylic-covered greenhouse in Carleton, Mich. and under cultural practices typical of commercial *Calibrachoa* production. During the production of the plants, day and night temperatures ranged from 18° C. to 24° C. Plants were twelve weeks from planting rooted cuttings when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCAL51505'.

Parentage:

*Female, or seed, parent*.—Proprietary seedling selection of *Calibrachoa* sp. identified as code number CJ08-07, not patented

*Male, or pollen, parent*.—Proprietary seedling selection of *Calibrachoa* sp. identified as code number CC016-01, not patented.

Propagation:

*Type*.—By vegetative terminal cuttings.

*Time to initiate roots, summer*.—About five to seven days at ambient temperatures ranging from 17° C. to 29° C.

*Time to initiate roots, winter*.—About seven to ten days at ambient temperatures ranging from 17° C. to 21° C.

*Time to produce a rooted plant, summer*.—About four to five weeks at ambient temperatures ranging from 17° C. to 29° C.

*Time to produce a rooted plant, winter*.—About five to six weeks at ambient temperatures ranging from 17° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, upright to outwardly spreading and mounding to trailing plant habit; moderately vigorous growth habit; moderate growth rate; freely branching habit with about four primary lateral branches each with about five to six secondary branches; dense and bushy appearance.

*Plant height, soil level to top of foliar plane*.—About 9.5 cm.

*Plant height, soil level to top of floral plane*.—About 11.5 cm.

*Plant diameter*.—About 21.5 cm.

Lateral branch description:

*Length*.—About 13.5 cm.

*Diameter*.—About 2 mm.

*Internode length*.—About 1 cm.

*Strength*.—Strong; wiry.

*Aspect*.—About 45° from stem axis.

*Texture and luster*.—Minute pubescence; matte.

*Color, developing*.—Close to 144B; at the internodes, close to 144B.

*Color, developed*.—Close to 146C.

Leaf description:

*Arrangement*.—Before flowering, alternate; after flowering, opposite; leaves simple.

*Length*.—About 2.6 cm.

*Width*.—About 1 cm.

*Shape*.—Elliptical.

*Apex*.—Rounded.

*Base*.—Attenuate.

*Margin*.—Entire.

*Texture and luster, upper and lower surfaces*.—Minute pubescence; matte.

*Venation pattern*.—Pinnate; arcuate.

*Color*.—Developing leaves, upper and lower surfaces: Close to 146A. Fully expanded leaves, upper surface: Close to 137A; venation, close to 146B. Fully expanded leaves, lower surface: Close to 147B; venation, close to 147C.

*Petioles*.—Length: About 5 mm. Diameter: About 2 mm. Strength: Moderately strong. Texture and luster, upper and lower surfaces: Minute pubescence; matte. Color, upper surface: Close to 146C. Color, lower surface: Close to 146D.

Flower description:

*Flower type and flowering habit*.—Double-type flowers arising from leaf axils; freely flowering habit with typically more than 300 flowers and flower buds developing per plant; flowers face mostly upright and then to outwardly with development.

*Fragrance*.—None detected.

*Natural flowering season*.—Plants of the new *Calibrachoa* begin flowering about six weeks after planting; plants flower continuously from the spring though the summer until frost.

*Flower longevity*.—Individual flowers last about four to five days on the plant; flowers persistent.

*Flower buds*.—Length: About 2.1 cm. Diameter: About 5 mm. Shape: Oblong, elongate. Texture and luster: Mostly smooth with minute pubescence along the veins; matte. Color: Close to 2C.

*Flower diameter*.—About 2.5 cm.

*Flower length* (*height*).—About 2.4 cm.

*Flower throat diameter*.—About 2 mm; inconspicuous.

*Flower tube length*.—About 1.8 cm.

*Flower tube diameter*.—About 6 mm.

*Corolla*.—Arrangement: A single whorl of five fused petals and five separate petaloids (transformed stamens) forming a rose-shaped flower. Petal lobe length (from throat): About 1.2 cm. Petal lobe width: About 1.4 cm. Petal shape: Fan-shaped. Petal apex: Rounded. Petal base: Fused. Petal margin: Entire; slightly undulate. Petal texture and luster, upper surface: Smooth, glabrous, satiny; somewhat glossy. Petal texture and luster, lower surface: Smooth, glabrous; matte. Petaloid lobe length (from throat): About 2 cm. Petaloid lobe width: About 1.4 cm. Petaloid shape: Rounded to somewhat claw-like. Petaloid apex: Rounded. Petaloid base: Attenuate. Petaloid margin: Entire; slightly undulate. Petaloid texture and luster, upper surface: Smooth, glabrous, satiny; matte Petaloid texture and luster, lower surface: Smooth, glabrous; matte. Throat texture and luster: Smooth, glabrous; slightly glossy. Tube texture and luster: Minute pubescence; matte. Color: Petal lobe, when opening, upper surface: Close to 4C to 4D. Petal lobe, when opening, lower surface: Close to 4D. Petal lobe, fully opened, upper surface: Close to 4D; venation, close to 145C; color becoming closer to 155A to 155B with development. Petal lobe, fully opened, lower surface: Close to 4D; venation, close to 145B; color becoming closer to 155A to 155B with development. Petaloid lobe, when opening, upper surface: Close to 4C to 4D. Petaloid lobe, when opening, lower surface: Close to 4D. Petaloid lobe, fully opened, upper surface: Close to 4D; venation, close to 145C; color becoming closer to NN155A with development. Petaloid lobe, fully opened, lower surface: Close to 155A; venation, close to 145C; color becoming closer to NN155A with development. Throat: Close to 2A to 2B; venation, close to 145C. Tube: Close to 4C; venation, close to 145C.

*Calyx*.—Arrangement: Star-shaped calyx tube with five sepals fused towards the base and arranged in a single whorl. Length: About 1.5 cm. Diameter: About 1.2 cm. Sepal length: About 7 mm. Sepal width: About 2 mm. Sepal shape: Lanceolate to ligulate. Sepal apex: Rounded to acute. Sepal margin: Entire. Sepal texture and luster, upper and lower surfaces: Minute pubescence; matte. Sepal color, when developing, upper and lower surfaces: Close to 144A. Sepal color, developed, upper and lower surfaces: Close to 144A.

*Peduncles*.—Length: About 1.1 cm. Diameter: About 1 mm. Angle: About 45° to 60° from stem axis. Strength: Moderately strong. Texture and luster: Minute pubescence; matte. Color: Close to 145A.

*Reproductive organs*.—Stamens: To date, none observed; all transformed into petaloids. Pistils: Quantity: One per flower. Pistil length: About 8 mm. Style length: About 5 mm. Style color: Close to 145C. Stigma diameter: Less than 1 mm. Stigma shape: Round. Stigma color: Close to 145A. Ovary color: Close to 145A. Seeds and fruits: To date, seed and fruit development have not been observed on plants of the new *Calibrachoa*.

Garden performance: Plants of the new *Calibrachoa* have been observed to have good garden performance and tolerate wind, rain and to be suitable for USDA Hardiness Zones 9a to 11b.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'USCAL51505' as illustrated and described.

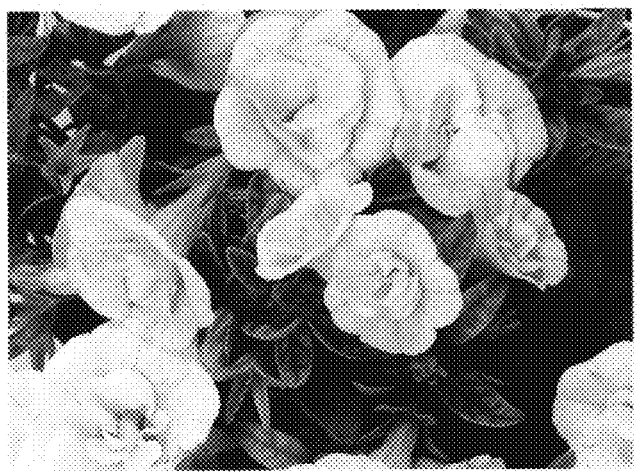
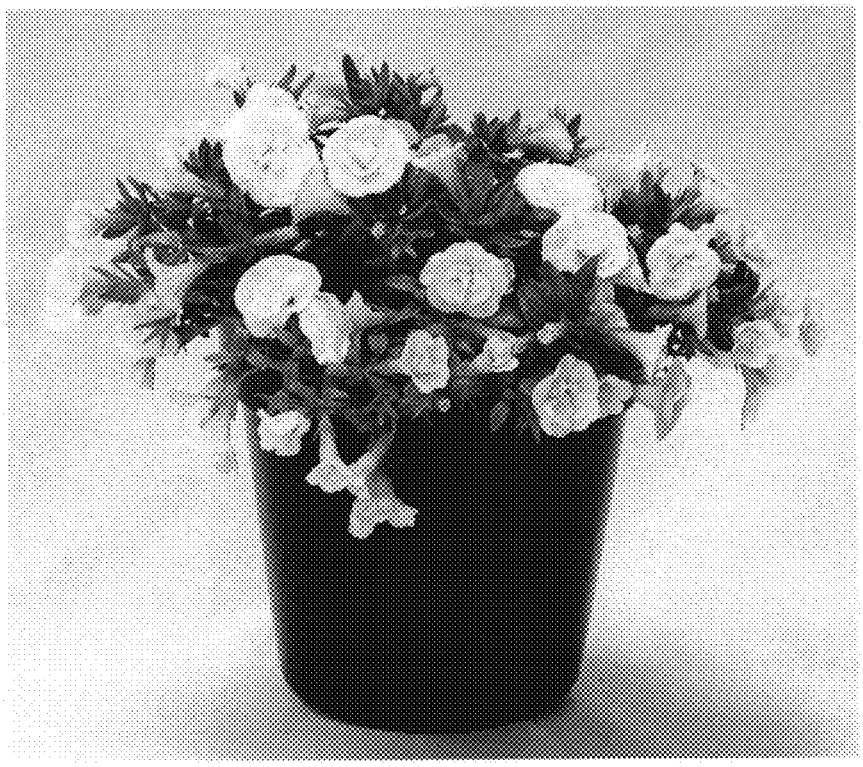

* * * * *